United States Patent
Hovland et al.

(10) Patent No.: US 10,328,273 B2
(45) Date of Patent: Jun. 25, 2019

(54) IMPLANTABLE MEDICAL DEVICES WITH ELECTRICALLY ISOLATED BATTERIES IN A SEPARATE ENCLOSURE

(71) Applicant: MEDTRONIC, INC., Minneapolis, MN (US)

(72) Inventors: Erik J. Hovland, Minnetonka, MN (US); Rajesh V. Iyer, Eden Prairie, MN (US); Steven J. May, Minnetonka, MN (US); Gordon O. Munns, Stacy, MN (US); Wesley A. Santa, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/936,942

(22) Filed: Nov. 10, 2015

(65) Prior Publication Data
US 2016/0129264 A1  May 12, 2016

Related U.S. Application Data

(60) Provisional application No. 62/078,673, filed on Nov. 12, 2014.

(51) Int. Cl.
*A61N 1/378* (2006.01)
*H01M 2/30* (2006.01)
(Continued)

(52) U.S. Cl.
CPC .............. *A61N 1/378* (2013.01); *A61N 1/375* (2013.01); *H01M 2/1022* (2013.01); *H01M 2/30* (2013.01); *H01M 2220/30* (2013.01)

(58) Field of Classification Search
CPC ....... A61N 1/375; A61N 1/3758; A61N 1/378
See application file for complete search history.

(56) References Cited

U.S. PATENT DOCUMENTS 4,010,760 A * 3/1977 Kraska ................... A61N 1/378
439/271
4,119,103 A * 10/1978 Jirak ...................... A61N 1/378
607/9

(Continued)

FOREIGN PATENT DOCUMENTS

| DE | 202010012164 | * 11/2010 | ............. A61N 1/375 |
| DE | 202010012164 U1 | 11/2010 | |
| EP | 2036589 A1 | 3/2009 | |

OTHER PUBLICATIONS

PCT/US2015/059868 International Search Report—dated May 18, 2016.
(Continued)

*Primary Examiner* — Eugene T Wu
(74) *Attorney, Agent, or Firm* — Withers & Keys, LLC

(57) ABSTRACT

Medical devices include a separate enclosure that houses a battery and electrically isolates the battery from external conditions such as any metal enclosures and ultimately isolates the battery from body fluids. Thus, the separate enclosure attaches to a housing of a medical device and provides for modularity of the battery which allows, for instance, different size batteries to be used with the same medical device design. The separate enclosure further prevents stimulation current from leaking back to the battery housing by providing the electrical isolation.

6 Claims, 10 Drawing Sheets

(51) Int. Cl.
*H01M 2/10* (2006.01)
*A61N 1/375* (2006.01)

(56) References Cited

U.S. PATENT DOCUMENTS

| | | | | |
|---|---|---|---|---|
| 5,314,451 A * | 5/1994 | Mulier | ............... | A61N 1/378 607/33 |
| 5,411,538 A * | 5/1995 | Lin | ............... | A61N 1/375 607/33 |
| 5,573,551 A * | 11/1996 | Lin | ............... | A61N 1/375 607/2 |
| 5,814,091 A * | 9/1998 | Dahlberg | ............... | A61N 1/375 607/36 |
| 6,269,266 B1 * | 7/2001 | Leysieffer | ............... | H04R 25/554 607/2 |
| 7,337,002 B2 * | 2/2008 | Gramse | ............... | A61N 1/375 607/33 |
| 7,376,465 B2 * | 5/2008 | Hornfeldt | ............... | A61N 1/375 607/116 |
| 7,647,110 B2 * | 1/2010 | Hornfeldt | ............... | A61N 1/375 607/116 |
| 9,220,902 B2 * | 12/2015 | Ries | ............... | A61N 1/362 |
| 9,457,195 B2 * | 10/2016 | Slavin | ............... | A61N 1/375 |
| 2003/0040781 A1 * | 2/2003 | Larson | ............... | A61N 1/375 607/36 |
| 2005/0043769 A1 * | 2/2005 | Gramse | ............... | A61N 1/375 607/36 |
| 2005/0159752 A1 * | 7/2005 | Walker | ............... | A61B 17/142 606/80 |
| 2005/0228456 A1 * | 10/2005 | Hornfeldt | ............... | A61N 1/375 607/36 |
| 2007/0150020 A1 * | 6/2007 | Hokanson | ............... | A61N 1/378 607/30 |
| 2007/0208384 A1 * | 9/2007 | Hoernfeldt | ............... | A61N 1/375 607/2 |
| 2007/0254212 A1 * | 11/2007 | Viavattine | ............... | A61N 1/375 429/164 |
| 2008/0109044 A1 * | 5/2008 | Gramse | ............... | A61N 1/375 607/36 |
| 2009/0075167 A1 | 3/2009 | Traulsen et al. | | |
| 2012/0107670 A1 * | 5/2012 | Viavattine | ............... | A61N 1/378 429/153 |
| 2012/0205150 A1 * | 8/2012 | Pretzlaff | ............... | A61N 1/3754 174/650 |
| 2014/0194953 A1 * | 7/2014 | Slavin | ............... | A61N 1/375 607/66 |
| 2015/0165196 A1 * | 6/2015 | Ries | ............... | A61N 1/362 607/119 |

OTHER PUBLICATIONS

PCT/US2015/059888 Written Opinion of the International Search Authority—dated May 18, 2016.

* cited by examiner

IMPLANTABLE MEDICAL DEVICES WITH ELECTRICALLY ISOLATED BATTERIES IN A SEPARATE ENCLOSURE

TECHNICAL FIELD

Embodiments relate to implantable medical devices that utilize battery power. More particularly, embodiments relate to implantable medical devices that utilize a battery that is located within a separate enclosure from other components of the medical device.

BACKGROUND

Implantable medical devices utilize electrical power to function when performing a medical task such as electrical stimulation therapy. In order to provide the implantable medical device with autonomy from any external power source, an internal battery may be included to provide the electrical power. Conventionally, the battery is positioned within a hermetically sealed enclosure together with circuitry for controlling the operation of the medical device.

The battery used for medical devices has an anode terminal and a cathode terminal but may also have an electrical potential relative to the anode and/or cathode that is present on a housing of the battery, particularly where the battery is a case neutral design. When the battery is mounted within the hermetically sealed enclosure of the implantable medical device, the battery housing is electrically isolated from the anode and/or cathode terminals as is appropriate. The battery is also electrically isolated from other electrical components of the medical device including an enclosure of the medical device and also electrical stimulation outputs. Likewise, the battery is isolated from related electrodes present on a medical lead that may be electrically connected to the electrical stimulation outputs.

While having the battery within the hermetically sealed enclosure provides electrical isolation for the battery, there is a lack of modularity. For instance, if a larger sized battery is desired, the medical device that is designed to house the smaller battery may not be able to easily accommodate the larger battery. Thus, conventional designs do not provide adequate modularity while providing electrical isolation of the battery housing.

SUMMARY

Embodiments address issues such as these and others by providing a separate enclosure for the battery that may be attached to the enclosure of the medical device to provide modularity. Thus, the separate enclosure may be constructed as necessary to accommodate the desired battery while the medical device may remain the same. Furthermore, the separate enclosure may insulate the battery housing from external conditions.

Embodiments provide a method of electrically isolating a battery of a medical device. The method involves providing an outer enclosure, providing an insulation enclosure, and placing the battery inside of the insulation enclosure where the battery has battery terminals. The method further involves placing the insulation enclosure inside of the outer enclosure and coupling the outer enclosure to the medical device while the battery is inside of the insulation enclosure and while the insulation enclosure is inside of the outer enclosure. The battery terminals extend beyond the insulation enclosure and outer enclosure and into the medical device.

Embodiments provide a medical device that includes a metal housing and circuitry within the metal housing. The medical device further includes an outer enclosure coupled to the metal housing and an insulation enclosure inside of the outer enclosure. The medical device also includes a battery inside of the insulation enclosure, and the battery has battery terminals that extend beyond the insulation enclosure and the outer enclosure and into the medical device and are electrically coupled to the circuitry.

Embodiments provide a method of electrically isolating a battery of a medical device that involves providing an insulation enclosure and providing the battery inside of the insulation enclosure where the battery has battery terminals. The method further involves providing an adapter plate attached to the insulation enclosure and attaching the adapter plate to the medical device while the battery is inside of the insulation enclosure and while the insulation enclosure is attached to the adapter plate with the battery terminals extending beyond the insulation enclosure and the adapter plate and into the medical device.

Embodiments provide a medical device that includes a metal housing, circuitry within the metal housing, an adapter plate attached to the metal housing, and an insulation enclosure attached to the adapter plate. The medical device further includes a battery inside of the insulation enclosure, the battery having battery terminals that extend beyond the insulation enclosure and the adapter plate and into the medical device and are electrically coupled to the circuitry.

DETAILED DESCRIPTION

Embodiments provide medical devices with batteries positioned within a separate enclosure that is attached to the enclosure of the medical device. The separate enclosure allows for battery modularity while also providing an insulation to isolate the battery housing from external conditions which prevents the battery housing from acting as an electrode.

Figure 1:
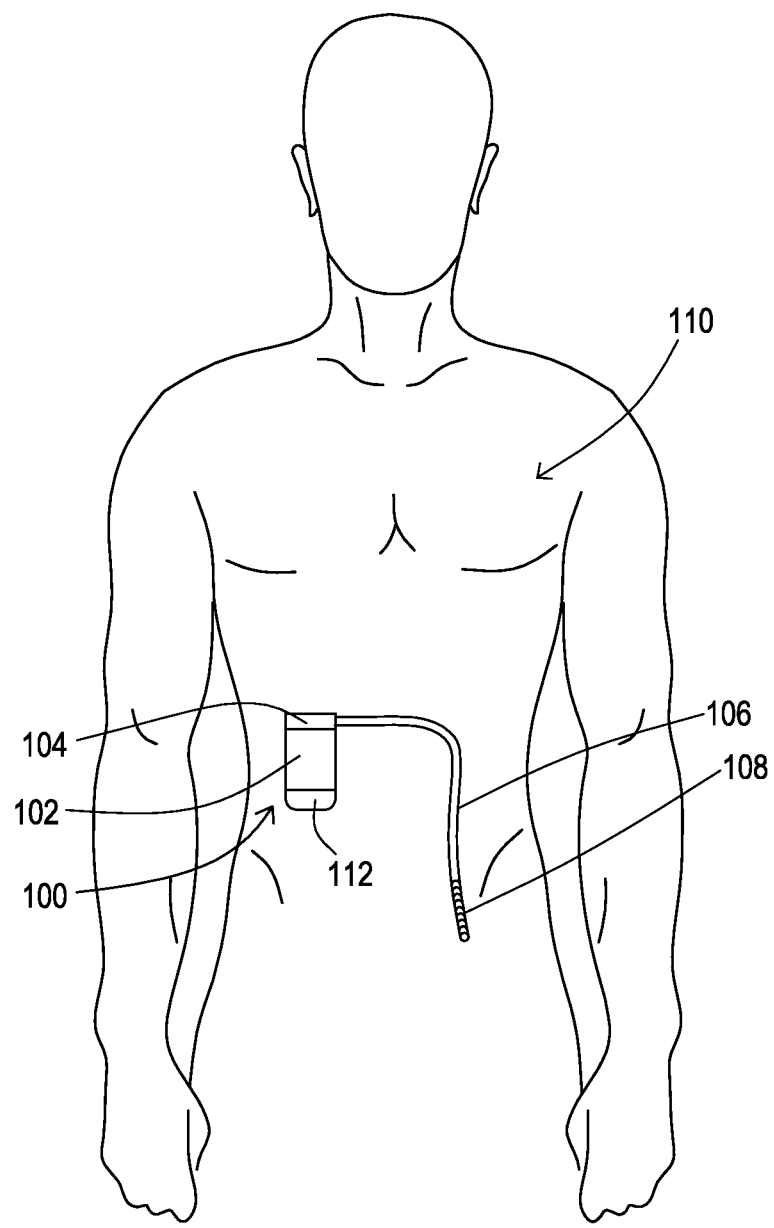
FIG. 1 shows an operating environment for various embodiments where a medical system including a medical device has a battery included in a separate enclosure that is attached to an enclosure of the medical device.

FIG. 1 shows a medical system 100 that includes a medical device 102 and a medical lead 106 that are implanted into a patient 110. In this particular example, the medical system 100 including the medical device 102 and the medical lead 106 are implantable. The medical lead 106 includes a proximal end that has been inserted into a bore of a header block 104 of the medical device 102. The distal end of the medical lead 106 includes electrodes 108 that are positioned at a target site where electrical stimulation therapy is to be provided. The medical device 102 is attached to a separate battery enclosure 112 that contains a battery that has a housing that is insulated from exterior conditions.

Figure 2:
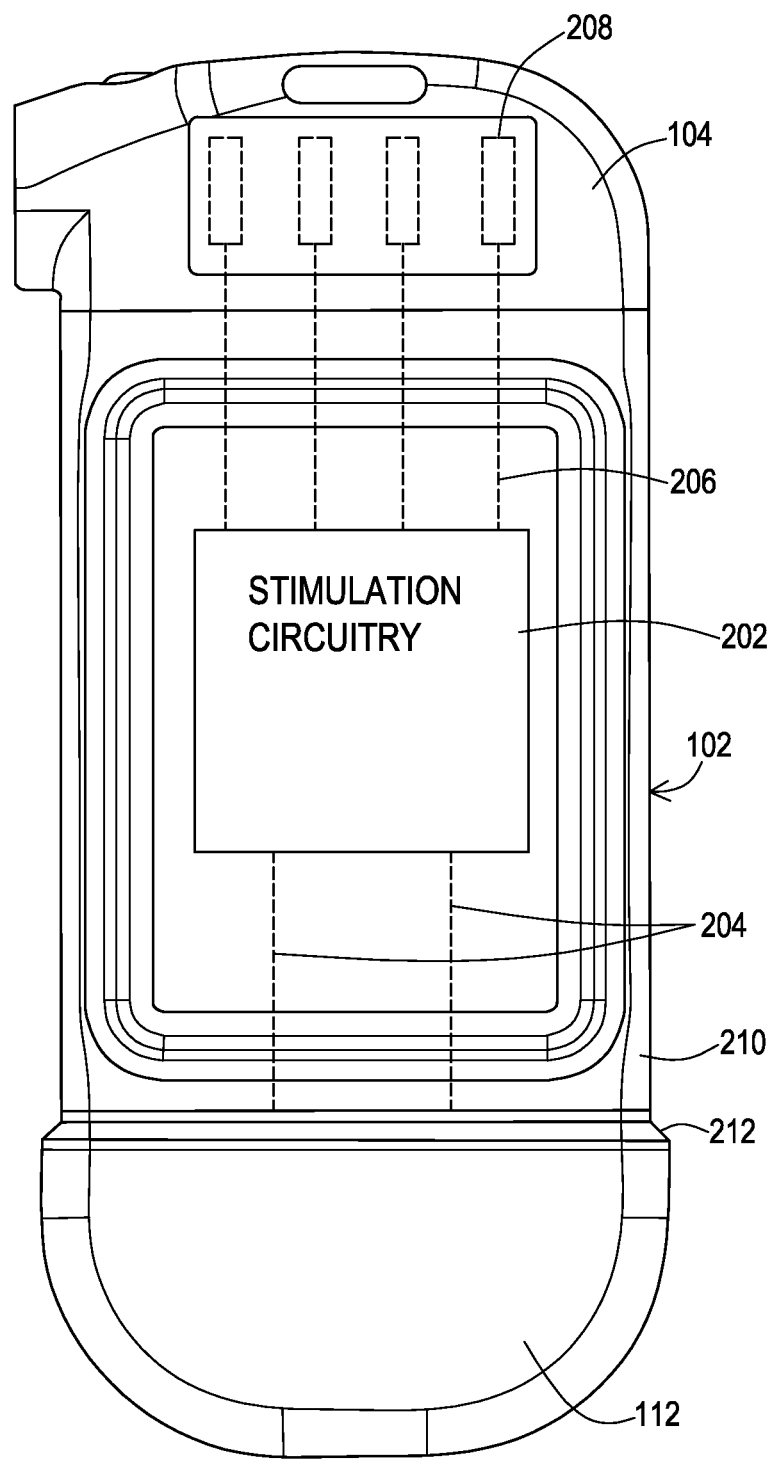
FIG. 2 shows an example of a medical device with a battery in a separate enclosure that is attached to the enclosure of the medical device.
Figure 3:
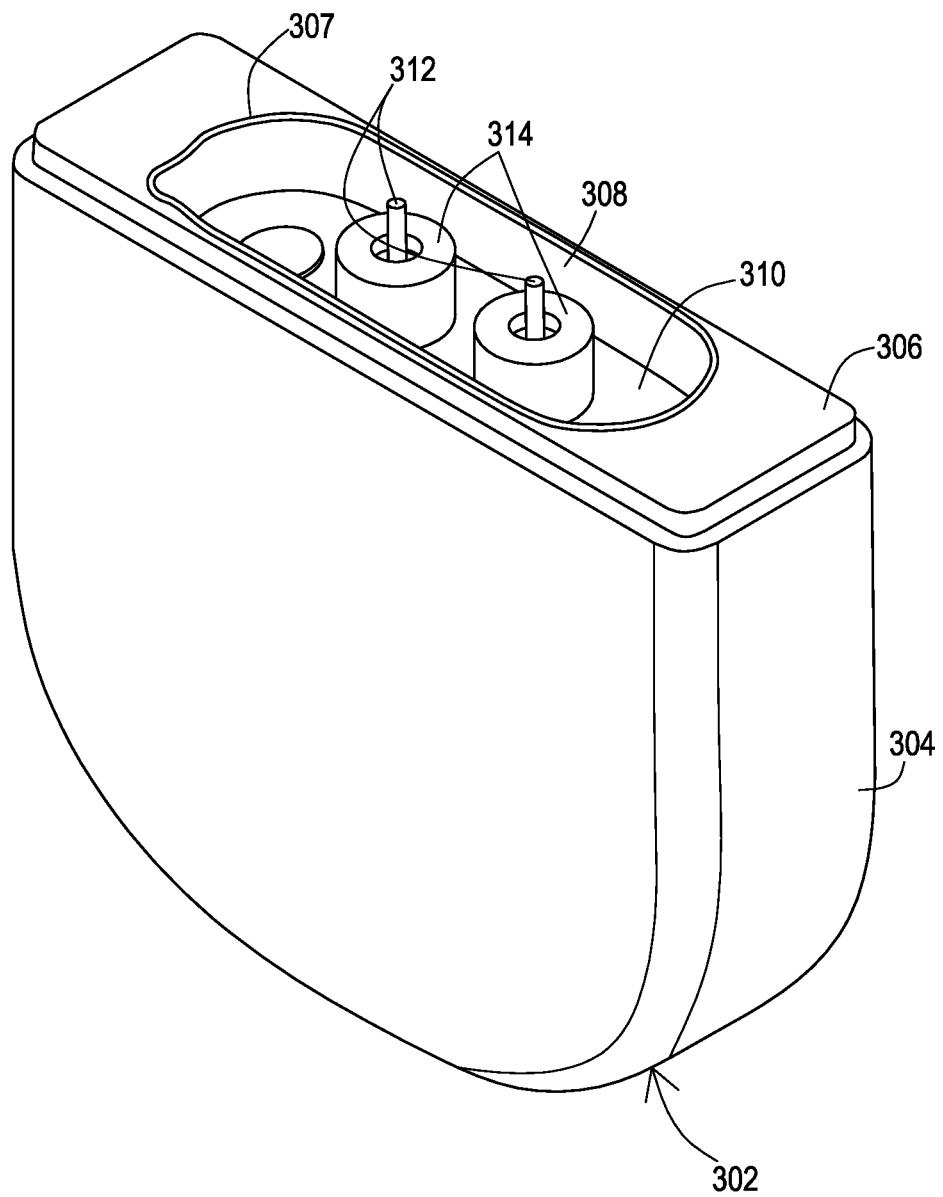
FIG. 3 shows a perspective view of one example of a battery in a separate enclosure.
Figure 4:
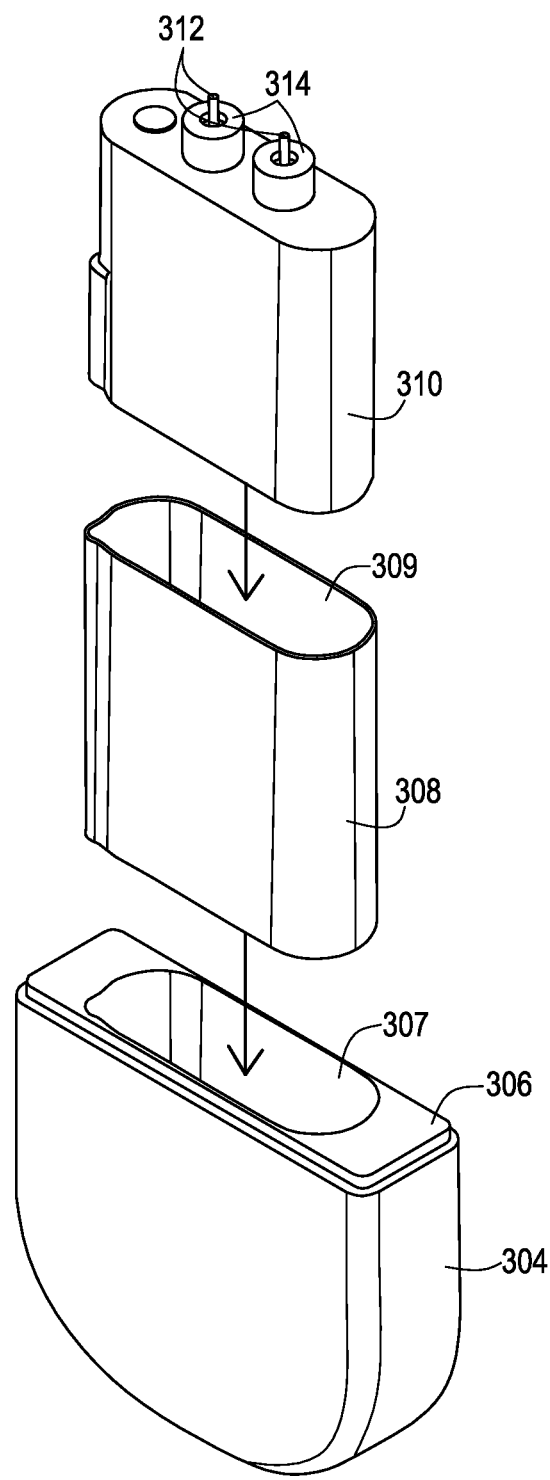
FIG. 4 shows an exploded view of the battery, an insulation enclosure, and an outer enclosure of the example of FIG. 3.
Figure 5A:
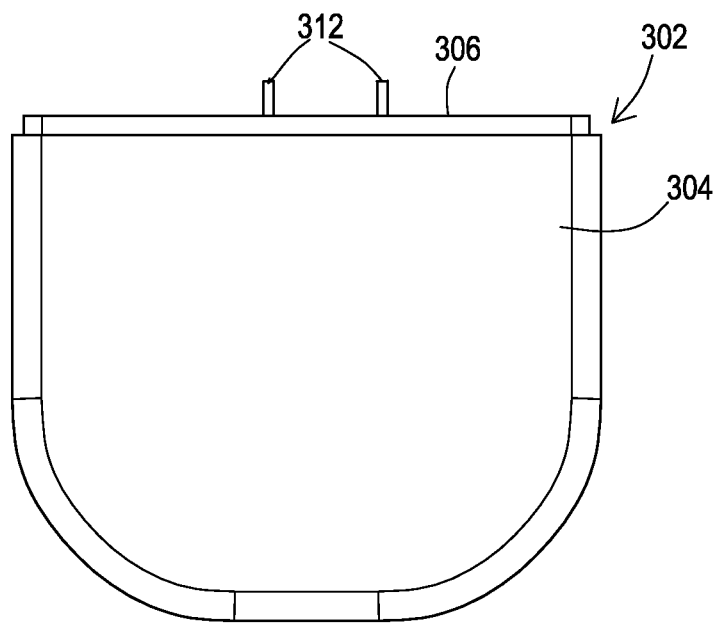
FIG. 5A shows a side view of the example of FIG. 3.
Figure 5B:
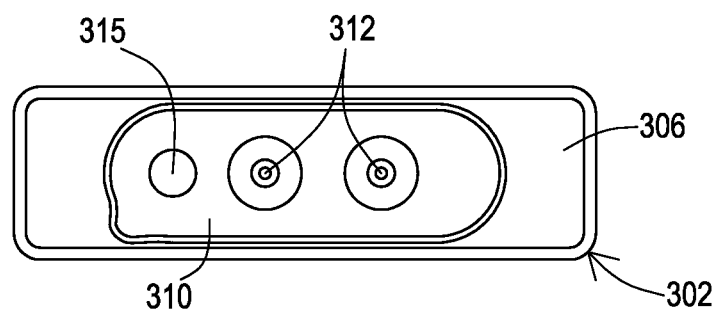
FIG. 5B shows a top view of the example of FIG. 3.

FIG. 2 shows an example of the medical device 102 and a header block 104 mounted on the medical device 102 for receiving the lead 106. The medical device 102 of this example includes stimulation circuitry 202 that provides electrical stimulation signals via a set of feed through conductors 206 that interconnect with corresponding electrical connectors 208 inside of the header block 104. The medical device 102 of this example also includes an enclosure 210 that encloses the stimulation circuitry 202.

The separate battery enclosure 112 is then attached to the enclosure 210. The separate battery enclosure 112 may include a plate, flange, or other structure 212 that allows the battery enclosure 112 to be laser seam welded to the enclosure 210. The top of the enclosure 112 may serve to cap the bottom of the enclosure 210 with the laser seam weld providing the hermetic seal. The top of the enclosure 112 may also provide apertures to allow battery terminal pins 204 to pass from inside the battery enclosure 112 to the interior of the enclosure 210 where the battery terminal pins 204 may then physically and electrically connect to the stimulation circuitry 202.

FIGS. 3, 4, 5A, and 5B show various views of one example of such a separate battery enclosure configuration 302. An outer enclosure 304 which may be constructed of various materials including biocompatible metals like Titanium, Niobium, alloys thereof, and the like. The outer enclosure 304 has a pocket 307 that has a depth that fully receives an insulation enclosure 308. The insulation enclosure 308 similarly defines a pocket 309 that has a depth that fully receives the battery 310. The insulation enclosure 308 may be constructed of various materials such as Polyimide, Polyether Ether Ketone (PEEK), Polysulphone, LCP etc.

As the battery 310 fits within the insulation enclosure 308 which then fits inside the outer enclosure 304, the battery 310 is both housed in the separate enclosure configuration 302 while being electrically isolated from the outer enclosure 304 of the separate enclosure configuration 302. Therefore, if the outer enclosure 304 is a conductor such as a biocompatible metal which is in contact with the body tissue and fluids, there will be no leakage of stimulation current directly back to the battery 310 because the insulation enclosure 308 provides the electrical isolation of the battery 310 from the outer enclosure 304. Such leakage current is particularly troubling for bipolar stimulation where the return path for the stimulation current should be through the lead rather than through tissue between the electrodes and the battery. Furthermore, the hermetic seal of the outer enclosure 304 that occurs between a top plate 306 and the medical device housing 210 of FIG. 2 prevents ingress of body fluids to the battery 310.

The battery 310 has terminal pins 312 that provide the cathode and anode terminals. In this particular example, the battery 310 also includes conductive ferrules 314 that are electrically isolated from the pins 312 by the presence of an insulator such as glass but are electrically connected to the battery housing to provide a feedthrough for the battery pins 312 to the interior of the enclosure 210. The terminal pins 312 extend out of the pocket defined by the insulative enclosure 308 and the outer enclosure 304 and into the housing 210 of FIG. 2. These pins are also electrically isolated from the external conditions by the hermetic seal of the top plate 306 of the outer enclosure 304 to the housing 210.

In this example, a plug 315 can also be seen on the battery 310. This plug 315 is present to provide a sealed closure to an opening in the battery housing that is used open when the battery 310 is being filled with electrolyte.

FIGS. 6, 7, 8A, and 8B show various views of a second example of a separate battery enclosure configuration 402. An outer enclosure 404 which may be constructed of various materials including biocompatible metals like Titanium, Niobium, alloys thereof, and the like. The outer enclosure 404 has a pocket 405 that has a depth that fully receives an insulation enclosure 408. The insulation enclosure 408 similarly defines a pocket 409 that has a depth that fully receives the battery 410. The insulation enclosure 408 may be constructed of various materials such as Polyimide, PEEK, Polysulphone, LCP etc.

As the battery 410 fits within the insulation enclosure 408 which then fits inside the outer enclosure 404, the battery 410 is both housed in the separate enclosure configuration 402 while being electrically isolated from the outer enclosure 404 of the separate enclosure configuration 402. Therefore, if the outer enclosure 404 is a conductor such as a biocompatible metal which is in contact with the body tissue and fluids, there will be no leakage of stimulation current directly back to the battery 410 because the insulation enclosure 408 provides the electrical isolation of the battery 410 from the outer enclosure 404.

Additionally, in this example, an adapter plate 406 and a top insulation layer 411 are provided. The top insulation layer 411 caps the top of the insulation enclosure 408 to electrically isolate the top of the battery 410 from the adapter plate 406. The adapter plate 406 is attached to the top edge of the outer enclosure 404, by a laser seam weld or similar manner of metal to metal connectivity to provide a hermetic seal, to fully enclose the insulation enclosure 408 and battery 410. The adapter plate 406 is also laser seam welded or otherwise attached to the bottom edge of the housing 210 of FIG. 2 to provide a hermetic seal to the housing 210.

Figure 6:
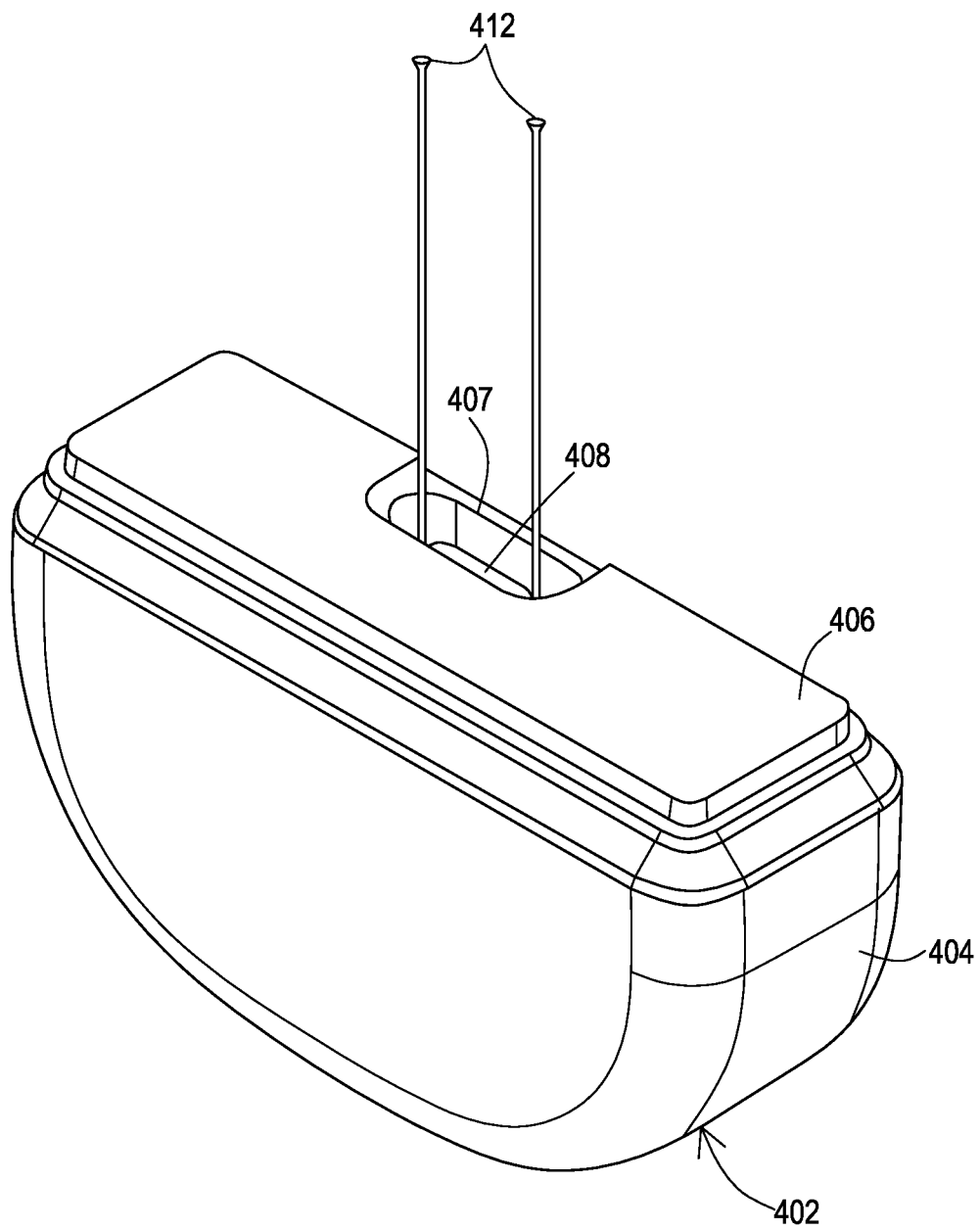
FIG. 6 shows a perspective view of a second example of a battery in a separate enclosure.
Figure 7:
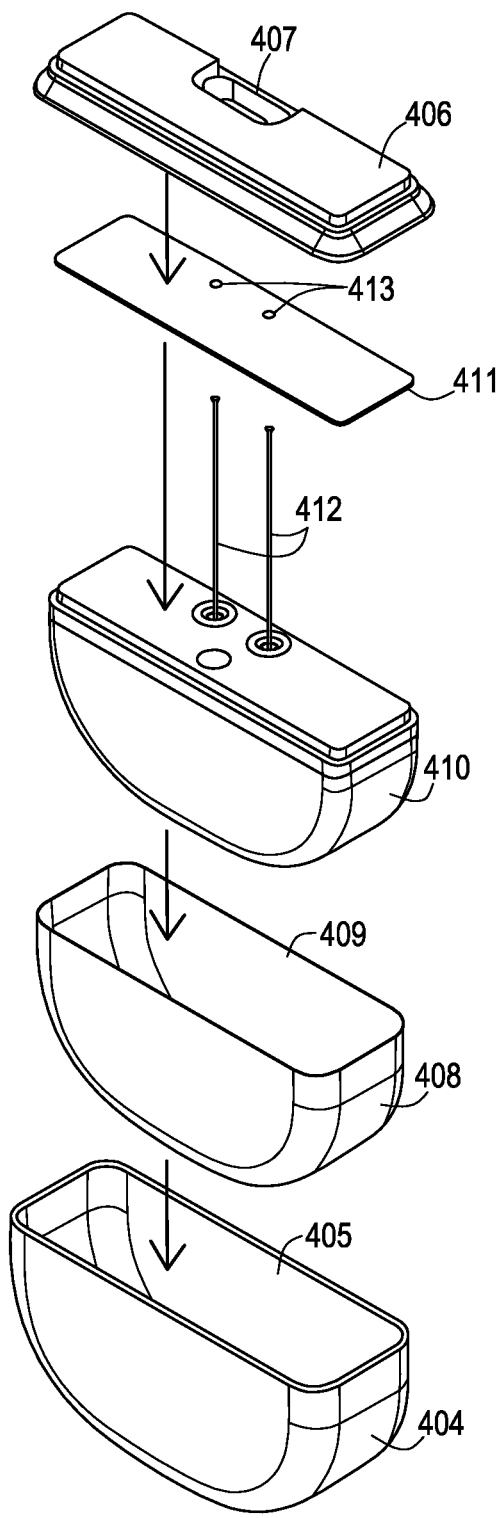
FIG. 7 shows an exploded view of the battery, an insulation enclosure, and an outer enclosure of the example of FIG. 6.
Figure 8A:
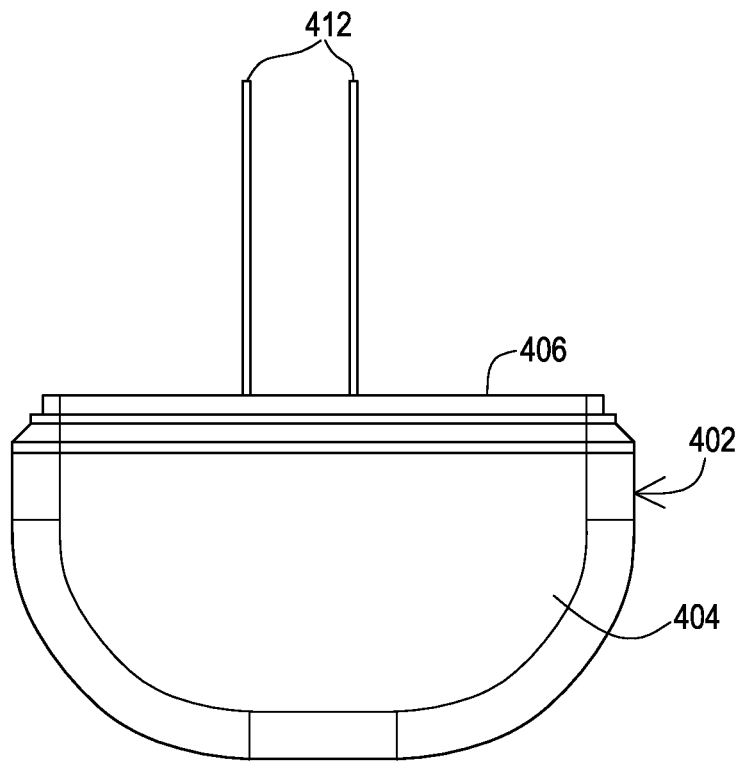
FIG. 8A shows a side view of the example of FIG. 6.
Figure 8B:
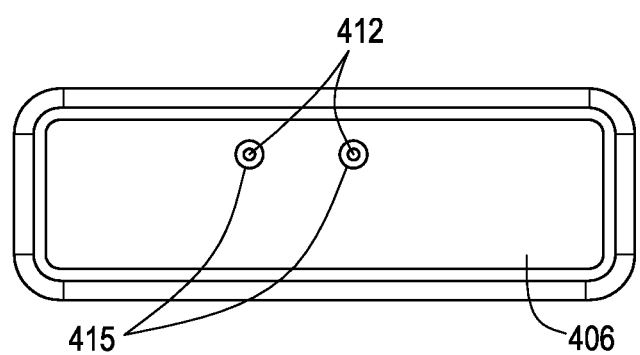
FIG. 8B shows a top view of the example of FIG. 6.

In order for the battery terminal pins 412 to reach the stimulation circuitry 202, the top insulation layer 411 includes holes 413 that allow the terminal pins to extend beyond the insulation enclosure 408. The adapter plate 406 also includes one or more openings 407 as shown in FIGS. 6 and 7 or openings 415 as shown in FIG. 8B that allow the terminal pins 412 to extend beyond the outer enclosure 404 and therefore exits the separate enclosure configuration 402 in order to extend into the housing 210 of the medical device 202.

The separate enclosure configuration 402 provides battery modularity while also electrically isolating the battery from the surrounding body tissues and fluid that are in contact with the exterior of the outer enclosure 404. As the battery 410 is contained within the insulative enclosure 408, the battery 410 is electrically isolated from the outer enclosure 404 so that the outer enclosure 404 may be constructed of an electrical conductor such as a biocompatible metal and the battery 410 remains electrically isolated from the body tissue and fluids.

Figure 9:
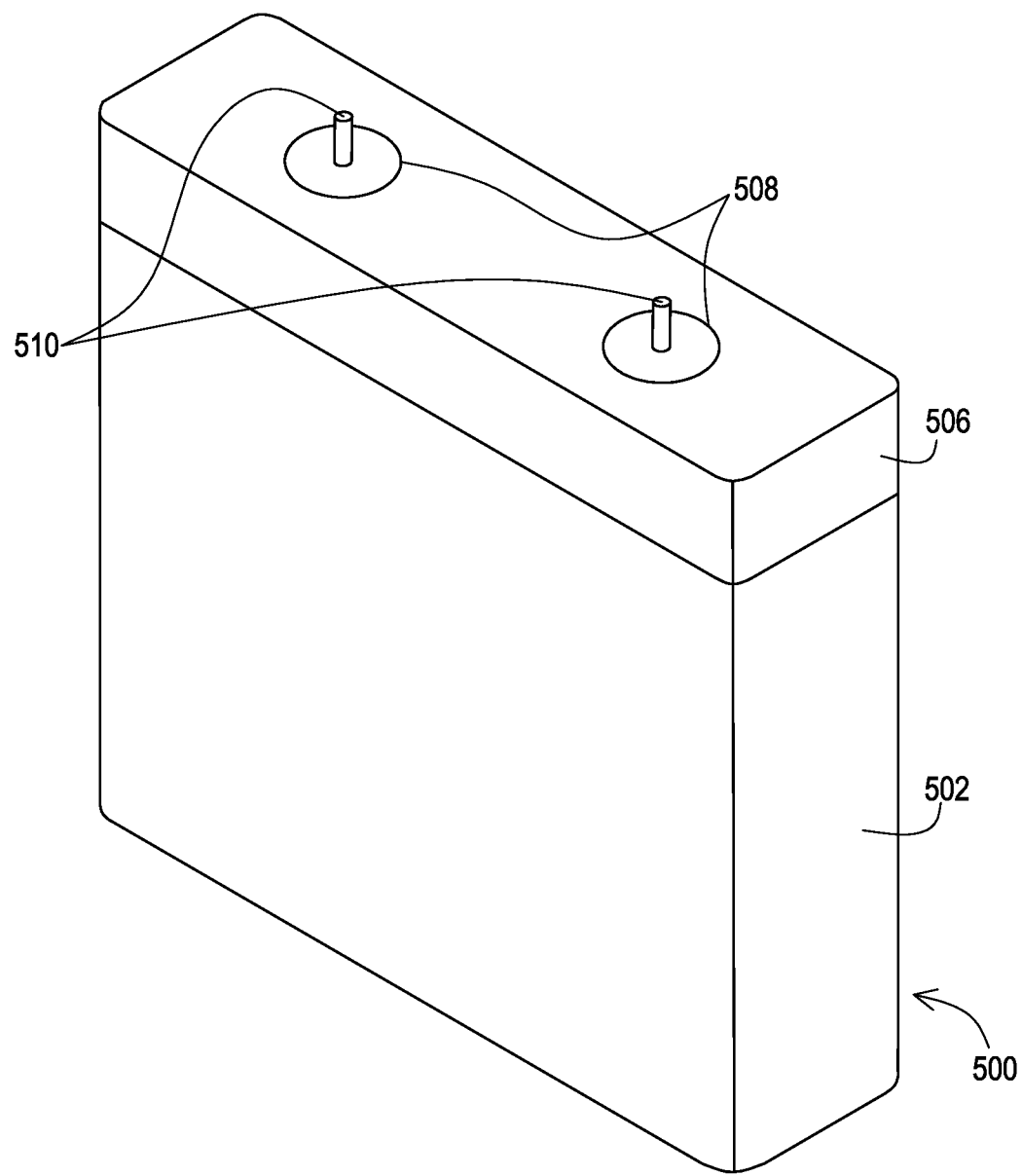
FIG. 9 shows a perspective view of a third example of a battery in a separate enclosure.
Figure 10A:
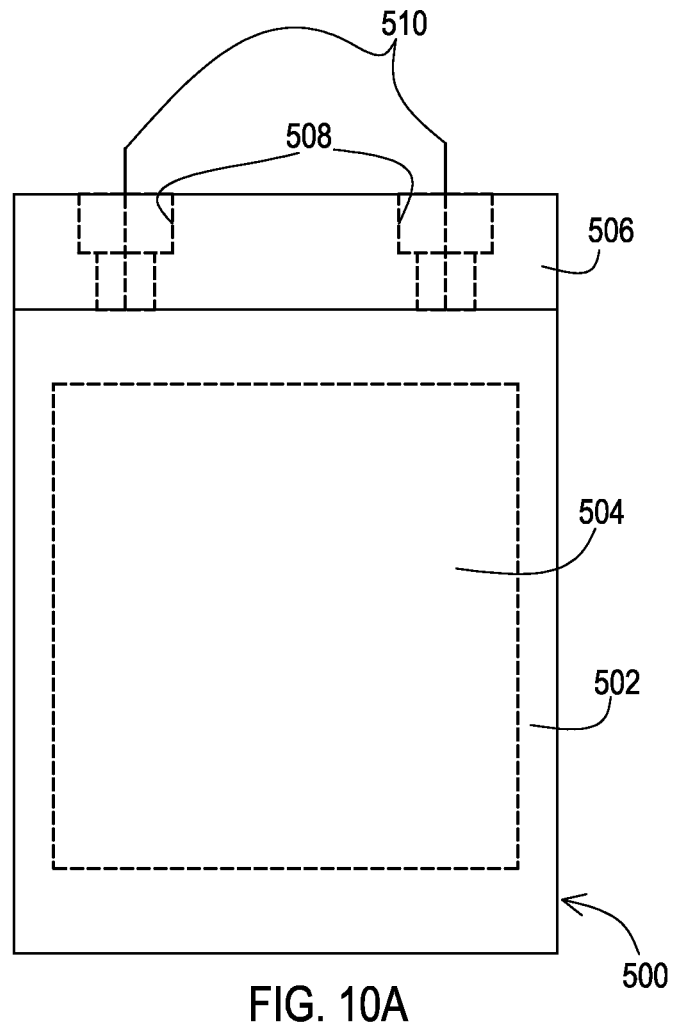
FIG. 10A shows a side view of the example of FIG. 9.
Figure 10B:
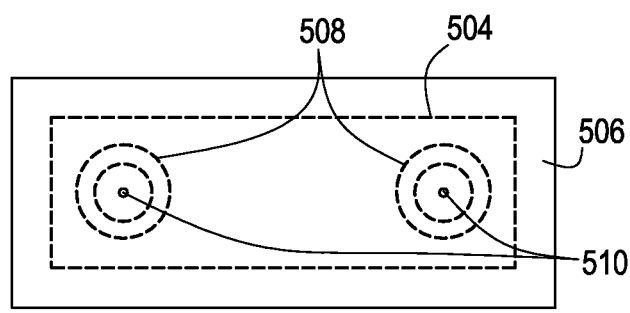
FIG. 10B shows a top view of the example of FIG. 9.

FIGS. 9, 10A, and 10B show various views of a third example of a separate battery enclosure configuration 500.

In this embodiment an outer insulative enclosure 502 is created by being overmolded around the battery 504. This outer insulative enclosure 502 may be constructed of various materials including biocompatible polymers such as PEEK, Polysulphone, LCP, Polyimide, Polyetherimide, etc. The outer insulative enclosure 502 fully encloses the battery 504 and because the outer insulative enclosure 502 is not an electrical conductor, the battery housing is electrically isolated from external conditions such as body fluids and tissue. Therefore, there will be no leakage of stimulation current directly back to the battery 504 because the insulation outer enclosure 502 provides the electrical isolation of the battery 504.

Additionally, in this example, an adapter plate 506 is provided. The adapter plate 506 is attached to the top edge of the outer insulation enclosure 502 to provide for attachment of the separate enclosure configuration 500 to the housing 210 of the medical device 202 of FIG. 2. The adapter plate 506 may be constructed of a biocompatible metal such as Titanium which allows the adapter plate 506 to be attached to the housing 210 by a laser seam weld or similar manner of metal to metal connectivity to provide a rigid connection and a hermetic seal.

To provide a robust connection of the overmolded outer insulation enclosure 502 to the adapter plate 506, the adapter plate 506 may include bores 508. These bores 508 may have a countersunk configuration as shown in FIG. 10A. When the overmolding about the battery is being performed to create the outer insulative enclosure 502, the overmolding may also include causing the insulative material of the enclosure 502 to flow into the bores 508. Once hardened, the insulative material of the enclosure 502 becomes rigidly connected to the adapter plate 506 via the presence within the bores 508.

In order for the battery terminal pins 510 to reach the stimulation circuitry 202, the terminal pins 510 extend beyond the outer insulation enclosure 504 and also extend through and beyond the bores 508 of the adapter plate 506. The overmolding of the insulation material surrounds the terminal pins 510 as they pass through and exit the bores 508. The terminal pins 510 extend from the bores 508 into the housing 210 of the medical device 202.

Thus, the separate enclosure configuration 500 also provides battery modularity while also electrically isolating the battery from the surrounding body tissues and fluid that are in contact with the exterior of the outer enclosure 502. There may be circumstances where the separate enclosure configuration 500 that lacks the conductive outer enclosure may be more appropriate than the examples above that use the conductive outer enclosure configuration. Examples of these circumstances include situations where device costs are a concern and the conductive outer enclosure is omitted, and/or where device longevity being decreased due to the lack of the conductive outer enclosure is not a concern.

While embodiments have been particularly shown and described, it will be understood by those skilled in the art that various other changes in the form and details may be made therein without departing from the spirit and scope of the invention.

What is claimed is:

1. A method of electrically isolating a battery of an implantable medical device, comprising:
providing an implantable outer enclosure;
providing an insulation enclosure;
placing the battery inside of the insulation enclosure, the battery having battery terminals with conductive ferrules surrounding the battery terminals with an insulator between the conductive ferrules and the battery terminals;
placing the insulation enclosure inside of the outer enclosure; and
coupling the outer enclosure to a metal housing of the implantable medical device while the battery is inside of the insulation enclosure and while the insulation enclosure is inside of the outer enclosure with the battery terminals extending beyond the insulation enclosure and outer enclosure and into the metal housing of the implantable medical device, wherein the outer enclosure includes a top plate having an aperture to a pocket provided within the outer enclosure with the battery, insulation enclosure, and conductive ferrules being positioned within the pocket, the top plate having an outer surface defining a plane, the plane having a first dimension and a second dimension perpendicular to the first dimension, the top plate providing a first area creating a first amount of separation of an edge of the aperture at the first area to an outer edge of the top plate at the first area measured along the first dimension and the top plate providing a second area creating a second amount of separate of an edge of the aperture at the second area to the outer edge of the top plate at the second area measured along the second dimension, the first amount of separation being greater than the second amount of separation.

2. The method of claim 1, wherein the outer enclosure is constructed of a biocompatible metal.

3. The method of claim 1, wherein the insulation enclosure is constructed of a polymer.

4. An implantable medical device, comprising:
an implantable metal housing;
circuitry within the metal housing;
an implantable outer enclosure coupled to the implantable metal housing, the outer enclosure including a top plate having an aperture to a pocket provided within the outer enclosure, the top plate having an outer surface defining a plane, the plane having a first dimension and a second dimension perpendicular to the first dimension, the top plate providing a first area creating a first amount of separation of an edge of the aperture at the first area to an outer edge of the top plate at the first area measured along the first dimension and the top plate providing a second area creating a second amount of separation of an edge of the aperture at the second area to the outer edge of the top plate at the second area measured along the second dimension, the first amount of separation being greater than the second amount of separation;
an insulation enclosure inside of the outer enclosure and within the pocket;
a battery inside of the insulation enclosure and within the pocket, the battery having battery terminals that extend beyond the insulation enclosure and the outer enclosure and into the metal housing and are electrically coupled to the circuitry with conductive ferrules positioned within the pocket and surrounding the battery terminals with an insulator between the conductive ferrules and the battery terminals.

5. The medical device of claim 4, wherein the outer enclosure is constructed of a biocompatible metal.

6. The medical device of claim 4, wherein the insulation enclosure is constructed of a polymer.

* * * * *